Figure 1:
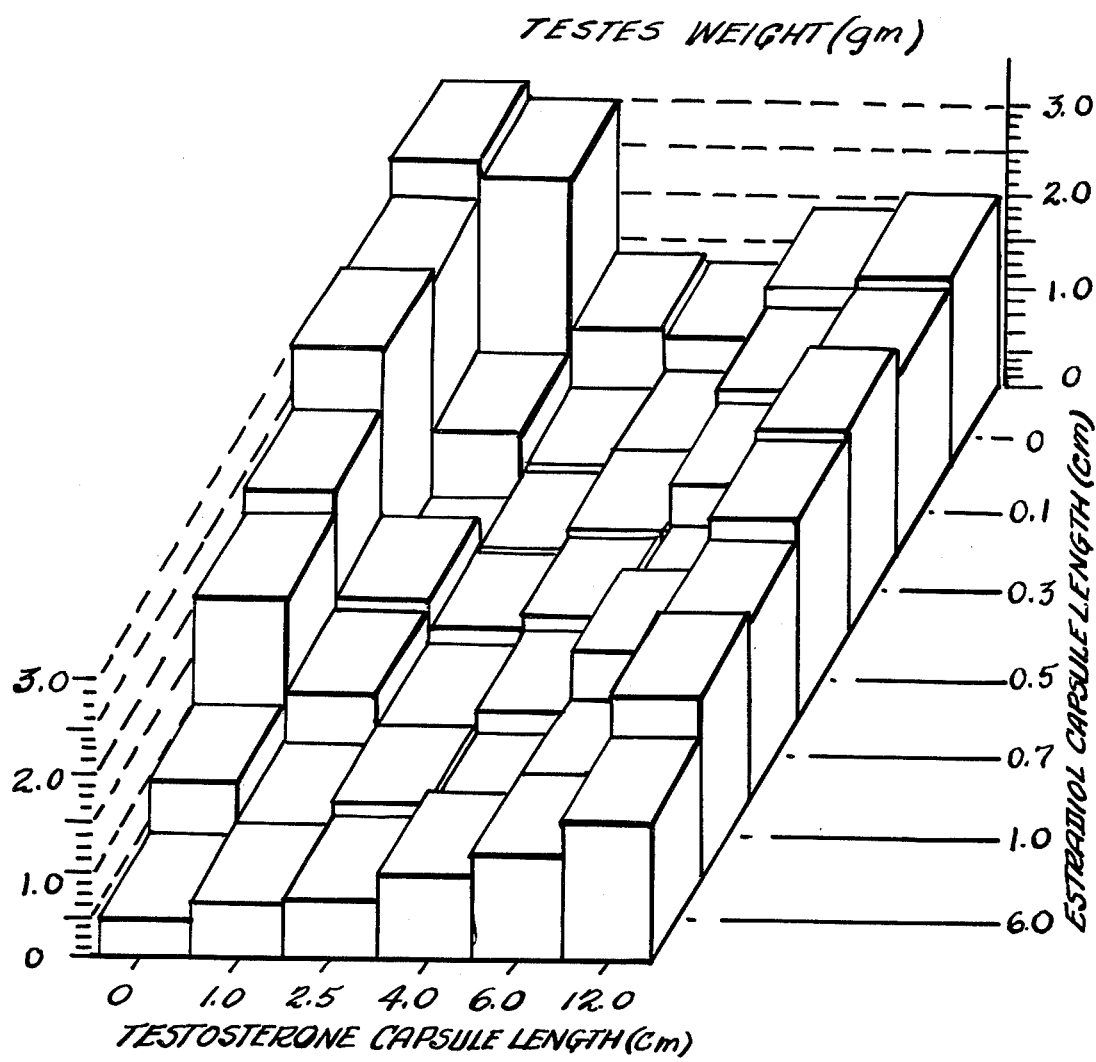

United States Patent [19]

Ewing et al.

[11] 4,210,644

[45] Jul. 1, 1980

[54] MALE CONTRACEPTION

[75] Inventors: Larry L. Ewing, Timonium, Md.; Claude Desjardins, Austin, Tex.

[73] Assignee: The Johns Hopkins University, Baltimore, Md.

[21] Appl. No.: 880,879

[22] Filed: Feb. 23, 1978

[51] Int. Cl.$^2$ ............................................. A61K 31/56
[52] U.S. Cl. .................................................... 424/239
[58] Field of Search ......................................... 424/239

[56] References Cited

U.S. PATENT DOCUMENTS 3,279,996   10/1966   Long et al. ............................ 424/33

OTHER PUBLICATIONS

Ewing, et al., Synergistic Interaction of Testosterone and Oestradiol . . . , *Nature,* vol. 269, No. 5627, pp. 409–411, Sep. 29, 1977.

Bishop, et al., Absorption of Hormone Implants in Man, *Lancet,* Aug. 11, 1951, pp. 229–232.

Kincl, et al., Sustained Release Hormonal Prep., A Survey of the Field, Excerpta Med. Int. Congr. (1973), pp. 977–981.

*Primary Examiner*—John M. Ford
*Assistant Examiner*—Robert C. Whittenbaugh
*Attorney, Agent, or Firm*—Cushman, Darby & Cushman

[57] ABSTRACT

A method of affecting male contraception which comprises subdermally implanting in the male an effective amount of an androgen and an estrogen in one or more slow release capsules. The combination of androgen and estrogen may also be used to enhance libido in an aging male.

6 Claims, 4 Drawing Figures

THE EFFECT OF TESTOSTERONE-ESTRADIOL TREATMENT UPON TESTES WEIGHT OF RATS. EACH BAR REPRESENTS THE MEAN OF 6 RATS.

THE EFFECT OF TESTOSTERONE-ESTRADIOL TREATMENT UPON SPERM PER RAT TESTES. EACH BAR REPRESENTS THE MEAN OF 6 RATS.

The effect of zero, 0.1 + 0.3 cm estradiol implants on sperm per testes in rats treated with 0, 1.0, 2.5 + 4.0 cm testosterone implants. Each point represents the mean of 6 rats.

THE EFFECT OF TESTOSTERONE-ESTRADIOL TREATMENT UPON VENTRAL PROSTATE WEIGHT IN RATS. EACH BAR REPRESENTS THE MEAN OF 6 RATS.

MALE CONTRACEPTION

The invention described herein was made in the course of work under a grant or award from the Department of Health, Education and Welfare.

The present invention is concerned with certain improvements in male contraception.

A great deal of work is going on to find effective contraceptive methods for men. Many different methods have been proposed and a few of these have met with some degree of success. For example, vasectomy is used fairly extensively for male contraception but there are some indications of possible undesirable side effects, e.g. high antibody buildup. Additionally, once a vasectomy has been performed, there is no real assurance that the resulting contraceptive effect can be reversed if this is later desired.

Methods involving the administration of contraceptive compounds, e.g. steroids, orally or by injection, offer the advantage of being reversible but undesired side effects can result and/or the activity of the contraceptive can be substantially diminished due to breakdown in the gut or metabolism thus requiring the administration of relatively large dosages to insure the contraceptive effect. Additionally, these methods require a disciplined and periodic administration of the contraceptive to be effective and, as a consequence, compliance with the necessary regimen is difficult to obtain or maintain.

The principal object of the present invention is to obviate problems previously encountered in male contraception. A more specific object of the invention is to provide for effective male contraception in a way which is readily reversible and yet can be continued for as long as desired without any compliance problem. Other objects will also be hereinafter evident.

Broadly stated, the present invention provides a method for male contraception which comprises subdermally implanting in the male one or more sustained release capsules which slowly but continuously release a combination of an androgen and an estrogen at a relatively constant rate for the desired length of time. Desirably, the androgen and estrogen are compounds which occur naturally in the male. The androgen testosterone and the estrogen estradiol are both produced in mamalian testes and are particularly suitable for use herein.

It has been found, according to the invention, that the subdermal implantation of testosterone and estradiol (or other functionally equivalent androgens and estrogens, respectively) in slow release capsules as described herein makes it possible to render the male reversibly infertile for as long as testosterone and estradiol are available for release from the implant.

An especially unique aspect of the invention is the finding that the testosterone and estradiol function synergistically to give a contraceptive effect which is not realized when the androgen or estrogen is used by itself even in larger amount than the combined amount of androgen and estrogen contemplated for use herein.

Another unique advantage of the invention is that use of the combination of androgen and estrogen as specified appears to depress anterior pituitary function and, therefore, spermatogenesis (i.e. contraception) without chronic elevation of the testosterone and estradiol content in the peripheral blood. The reasons for this are not fully understood but apparently the subdermal slow release of testosterone and estradiol as disclosed herein somehow prevents the usual generation of androgen and estrogen in the male testes. This is very surprising because the amounts of testosterone and estradiol which are released with implanted capsules according to the invention are considerably lower than the amounts normally generated in the testes.

The invention is thought to be applicable to combinations of any androgen and estrogen, whether synthetic or naturally occurring (i.e. produced in the human body). It is preferred, however, that combinations of naturally occurring androgens and estrogens be used and the invention is described hereinafter in detail using synergistic combinations of the preferred steroids, testosterone and estradiol, as the androgen and estrogen, respectively.

The testosterone and estradiol may be implanted as a mixture in one or more slow release capsules. Alternatively the testosterone and estradiol may be implanted separately in different capsules or in the same capsule but without being physically mixed together, for example, by compartmentalizing the capsule. Estradiol may also be administered by absorption from a sustained release device attached to the skin.

Implants according to the invention may be made subcutaneously at any convenient body location, e.g. on the back, arms or legs. Conventional implanting means may be used, for example, a large bore needle which releases the capsule under the skin.

Slow release capsules for use herein may be made with any suitable inert, nonreactive film- or tube-forming polymer or the like having suitable slow release properties. Such polymers are well known and commercially available. Typically, there may be used polydimethylsiloxane medical grade tubing which is available as "Silastic" (Dow Corning No. 602-305). This material has desirable slow release properties and capsules may be made therefrom by cutting the tubing to the desired length, closing one end of the cut tube, filling the same with the testosterone and/or estradiol and then closing the open end. The size and shape of the capsule and consequently the amount of testosterone and/or estradiol therein can be varied depending, for example, on the length of time desired for the contraceptive effect. It is contemplated, for example, that capsule sizes may be chosen to give the desired contraceptive effect for periods of from one month to 5 years and the size of the capsule will be selected accordingly. Since the testosterone should be administered at a greater rate than the estradiol, a smaller capsule can be used for the estradiol than for the testosterone when separate capsules are used to obtain the desired contraceptive effect.

The amounts of testosterone and estradiol released per day from the implanted capsule or capsules, according to the invention, can be fairly widely varied and will depend on the weight of the male involved. Typically, for a male rat of about 300 grams body weight, the amounts of testosterone and estradiol released per day may be in the order of 80 micrograms and 0.24 micrograms, respectively. For human male application, the implant or implants should be such as to release about 2 to 10 mg per day of testosterone and 5 to 40 micrograms per day of estradiol in the case of a male weighing about 70 kilos. It is to be noted in this regard that the average man produces about 7–10 mg per 24 hour day of testosterone and about 40 micrograms of estradiol. The daily administration of testosterone and estradiol according to the invention will usually be less than the amounts normally produced in the male. It will be appreciated, however, that amounts of testosterone and/or estradiol outside the indicated ranges may be necessary or desirable in certain cases and significant variations from these amounts may be necessary when androgens and estrogens other than testosterone and estradiol, respectively, are used.

It appears that the ratio of testosterone to estradiol should be kept within certain limits, generally in the range of 250–500 to 1. A ratio significantly below 250:1 may cause enlargement of the breasts and/or result in other feminizing signs while a ratio substantially above 500 may cause the combination to lose the synergistic effect which is otherwise obtainable. Here again, however, the range of useful ratios will vary depending on the specific androgens and estrogens involved, the indicated ratios for testosterone and estradiol being given as representative.

The invention is illustrated, but not limited, by the following examples using capsules made from Dow Corning #602-305 "Silastic" polydimethylsiloxane medical grade tubing (0.2 mm wall thickness, 3.18 mm outer diameter). Such capsules have previously been shown to release hormonal steroids, e.g. testosterone, at relatively constant rates over protracted time periods following subdermal placement (see Ewing et al *J. Reprod. Fertil.*, 35, 245–253, 1973, and Stratton et al, *J. Reprod. Fertil.*, 35, 235–244, 1973).

EXAMPLE 1

Ninety adult male Sprague-Dawley rats (225–260 g) were randomly assigned to one of fifteen treatment groups. Subdermal implants of polydimethylsiloxane capsules of differing sizes, containing either testosterone or estradiol-17β were used for steroid adminstration. Three groups of 30 rats each were given either no estradiol-17β or estradiol-17β filled implants measuring 0.1 cm or 0.3 cm in length (release rate of estradiol approximately 0.1 μg/cm/day). The 30 rats in each of these three treatment groups were further subdivided into five groups of 6 rats each, receiving either no testosterone or testosterone filled implants measuring 1.0, 2.5, 4.0 or 6.0 cm length (release rate for testosterone is approximately 30 μg/cm/day). The implants were prepared by filling the polydimethylsiloxane tubing with one of the steroids and were then implanted subcutaneously as previously described (see again *J. Reprod. Fertil.*, 35, pages 235–253 (1973). Three months after capsule implantation the rats were weighed, decapitated, trunk blood collected, and serum prepared for estradiol, testosterone, and LH radio-immunoassay using conventional techniques. The seminal vesicles and ventral prostate were dissected, freed of extraneous tissue and weighed; the fluid was expressed from seminal vesicles prior to weighing. The number of spermatids and spermatozoa were determined hemacytometrically from homogenates of testes from each animal. Testicular perfusions were done as described in *J. Reprod. Fert.*, 6, 1–8 (1963) and *Can. J. Biochem.*, 44, 1327–1344 (1966).

The average numbers of spermatozoa and spermatids in the rats treated with testosterone and/or estradiol according to the foregoing example are shown in the following Table 1:

Table 1

| Estradiol Implant Length (cm) | Testosterone Implant Length (cm) | | | | |
|---|---|---|---|---|---|
| | 0 | 1 | 2.5 | 4 | 6 |
| 0 | 234 ± 12* | 193 ± 9 | 61 ± 39 | 17 ± 6 | 80 ± 19 |
| 0.1 | 194 ± 18 | 38 ± 26 | <1' | 3.8 ± 2 | 85 ± 7 |
| 0.3 | 205 ± 15 | <1 | <1 | 3 ± 1 | 43 ± 11 |

*Each value represents the mean ± the standard error of six animals. This is also true for all other numerical values given in the various tables herein.
'Indistinguishable from zero.

Table 1 shows that testosterone administered in the absence of estradiol caused the expected biphasic changes in the combined number of spermatozoa and/or spermatids per testis (Berndtson et al, *J. Endocr.*, 62, 125–135, 1974). Spermatid and spermatozoa numbers did not reach zero in any of the five treatment groups. This latter result differs from that reported by Berndtson et al and probably results from the fact that spermatogenesis was quantified by counting germ cell numbers in histological sections of testes by Berndtson et al, whereas quantitation in the present example was achieved by counting nuclei of spermatid and spermatozoa in a testicular homogenate with a hemocytometer.

Table 1 also shows that no significant alterations in spermatogenesis were apparent in rats receiving estradiol administered in the absence of testosterone. Table 1, however, shows the surprising result that testosterone and estradiol dosages (e.g., 1.0 cm testosterone plus 0.1 cm estradiol) which failed to significantly inhibit spermatogenesis when administered alone, acted when used in combination to markedly inhibit spermatogenesis when given simultaneously. This interaction apparently is synergistic since increasing the dose of either steroid by more than two-fold did not result in the major suppression of spermatogenesis obtained by the combination of testosterone and estradiol.

Examination of the testes of each animal treated with several of the testosterone-estradiol combinations showed these to be devoid of condensed spermatids and spermatozoa. At the lower estradiol-17β dose (0.1 cm implant), azoospermia was first obtained with a 2.5 cm testosterone implant (Table 1). Consequently, further measurements were completed on animals receiving this steroid formulation.

Table 2 shows the effect of testosterone and estradiol subdermal implants on serum concentrations of luteinizing hormone, testosterone and estradiol and on the weight of the seminal vesicles and ventral prostrate in the rats:

Table 2

| CRITERIA MEASURED | TREATMENT | | | |
|---|---|---|---|---|
| | Control | 2.5cm Testosterone | .1cm Estradiol | 2.5cm Testosterone plus 0.1cm Estradiol |
| Luteinizing Hormone Δ (ng/ml) | 8.0 ± 1.0 | 2.9 ± 0.3 | 2.8 ± 0.4 | N.D.° |
| Testosterone (ng/ml) | 2.3 ± 0.5 | 3.0 ± 0.6 | 0.9 ± 0.5 | 2.2 ± 0.2 |
| Estradiol (pg/ml) | 45.8 ± 11.0 | 47.5 ± 11.0 | 46.2 ± 3.0 | 42.7 ± 4.0 |
| Paired Seminal Vesicle Weight (mg) | 454.0 ± 8.0 | 464.0 ± 26.0 | 258.0 ± 28.0 | 451.0 ± 21.0 |
| Ventral Prostrate Weight (mg) | 577.0 ± 62.0 | 686.0 ± 57.0 | 358.0 ± 36.0 | 678.0 ± 34.0 |

ΔExpressed in terms of nanogram equivalents/of NIAMD-Rat-LH-RP-1 per milliliter of blood serum. The rat LH standard has a relative potency of 0.03X NIH-LH-Sl in the ovarian ascorbic acid depletion assay.
°Nondetectable.

While the mechanism by which the testosterone-estradiol combination works to give the indicated results is not understood, the data in Table 2 suggest that the combination may inhibit spermatogenesis indirectly by suppressing immunoreactive LH release. However, a possible direct effect of estradiol on testosterone secretion cannot be ruled out since it has previously been suggested (*J. Endocrinol.,* 60, 375–376, 1974) that estrogen exerts a direct inhibitory effect on testicular steroidogenesis. Importantly, the serum concentration of testosterone and estradiol were similar to control, in rats receiving the combination of 2.5 cm testosterone and 0.1 cm estradiol implants (Table 2). That serum testosterone concentration mirrors the free biologically active hormone is seen by the fact that accessory sex organ weights in rats receiving the 2.5 cm testosterone plus 0.1 cm estradiol implants were not significantly different from control rats.

The results given in Tables 1 and 2 raise two important points regarding the mechanism by which testosterone-estradiol combinations induce azoospermia, since the circulating levels of each steroid remain within the range typically noted in the sera of untreated adult male rats. The first is concerned with the fact that peripheral blood serum testosterone and estradiol concentrations are not increased. The apparent reason for this is that testes of rats receiving the 2.5 cm testosterone-0.1 cm estradiol implants failed to produce testosterone. Testosterone secretion by in vitro perfused testes from control rats and rats receiving the 2.5 cm testosterone-0.1 cm estradiol implants were 5.0±S.E.M. 0.4 (n=6) and 0.1±0.03 S.E.M. (n=6) μg/hour. Thus, it can be concluded that the major source of testosterone in the peripheral blood of the aspermatogenic rats originated from the subdermal implant. The steroids released from the implants apparently replaced those usually derived directly from the testis or indirectly from peripheral conversion of testicular steroids. It would appear that testosterone emanating from the capsules was sufficient to maintain peripheral androgen dependent functions but insufficient to maintain the high intratesticular concentration of testosterone required for spermatogenesis.

The second point relates to the mechanism by which normal circulating titers of testosterone and estradiol completely suppressed circulating levels of immunoreactive LH. The apparent reason for this is that, in contrast to the episodic fluctuations in testosterone titers seen in normal males, the capsules release the steroids at relatively constant rates. Thus, it appears that sustained release of testosterone provides a more effective signal to androgen dependent target tissues than the episodic fluctuations characteristic of intact animals.

The foregoing indicates that azoospermia may be induced in adult male rats with the appropriate testosterone-estradiol formulations administered via a subdermal sustained release device. Furthermore, those azoospermic rats appear to remain sexually active although infertile thus indicating that treatment according to the invention does not materially reduce libido or sex drive.

EXAMPLE 2

Two hundred and fifty two male rats were randomly assigned to one of 42 treatment groups shown below. Six rats were assigned to each treatment group.

| Estradiol Capsule Length (CM) | Testosterone Capsule Length (CM) | | | | | |
|---|---|---|---|---|---|---|
| | 0 | 1.0 | 2.5 | 4.0 | 6.0 | 12.0 |
| 0 | 6 | 6 | 6 | 6 | 6 | 6 |
| 0.1 | 6 | 6 | 6 | 6 | 6 | 6 |
| 0.3 | 6 | 6 | 6 | 6 | 6 | 6 |
| 0.5 | 6 | 6 | 6 | 6 | 6 | 6 |
| 0.7 | 6 | 6 | 6 | 6 | 6 | 6 |
| 1.0 | 6 | 6 | 6 | 6 | 6 | 6 |
| 6.0 | 6 | 6 | 6 | 6 | 6 | 6 |

Three months after subdermal capsule placement, the rats were weighed, sacrified by decapitation with a guillotine, trunk blood collected, serum prepared and frozen for estradiol, testosterone, LH and FSH measurement. The capules were removed, cleaned, desicated for 24 hours and weighed to determine testosterone release rate. The estradiol release rate was not measured since this rate is so slow as to preclude gravimetric release rate measurement. Portions of testicular and ventral prostatic tissue were fixed in Zenker Formal solution. Testes, caput-corpus and cauda epididymis, seminal vesicle and ventral prostate weights were measured. Spermatid and spermatozoa numbers were determined hemacytometrically in homogenates of weighed portions of testicular, caput-corpus and cauda epididymal tissue from each animal.

The test results showed that the animals tolerated the capsules well in that no tissue inflammation, capsule loss or capsule migration was observed. The body weight of rats on all treatment groups increased. However, those rats receiving estradiol gained less weight than control rats or those receiving testosterone. Rats receiving estradiol ($E_2$) implants greater than 0.5 CM shows mammary gland stimulation since milk formation was observed. $E_2$ dosages causing this response should not be used for male contraceptive purposes.

Table 3 shows the effect of the testosterone and estradiol treatment on testis weight in rats, the weight being given in grams.

Table 3

| Estradiol Implant Length (CM) | Testosterone Implant Length (CM) | | | | | |
|---|---|---|---|---|---|---|
| | 0 | 1.0 | 2.5 | 4.0 | 6.0 | 12.0 |
| 0 | 3.4 ± .09 | 3.2 ± .14 | 1.6 ± .30 | 1.5 ± .08 | 2.0 ± .11 | 2.2 ± .37 |
| 0.1 | 3.0 ± .13 | 1.4 ± .34 | 1.0 ± .02 | 1.2 ± .10 | 1.8 ± .06 | 2.2 ± .07 |
| 0.3 | 3.1 ± .11 | 0.7 ± .06 | 0.9 ± .04 | 1.2 ± .06 | 1.7 ± .15 | 2.3 ± .17 |
| 0.5 | 2.4 ± .20 | 1.2 ± .27 | 0.9 ± .06 | 1.1 ± .08 | 1.1 ± .13 | 2.2 ± .05 |
| 0.7 | 2.1 ± .42 | 1.1 ± .33 | 0.8 ± .06 | 1.0 ± .05 | 1.6 ± .08 | 2.0 ± .20 |
| 1.0 | 1.0 ± .12 | 0.6 ± .03 | 0.8 ± .02 | 0.8 ± .06 | 1.1 ± .08 | 2.1 ± .11 |
| 6.0 | 0.5 ± .03 | 0.6 ± .04 | 0.7 ± .05 | 0.9 ± .12 | 1.1 ± .09 | 1.6 ± .12 |

As will be seen from Table 3, increasing the testosterone (T) dosage (0 through 12 CM) gave the normal biphasic response in testis weight declining from 3.4 g for control to 1.5 g for animals receiving 4.0 CM T capsules and increasing to 2.2 g for animals receiving 12 CM T capsules. As would be expected, testicular weight declined from 3.4 g for the control to 0.5 g for rats receiving 0 through 6.0 CM $E_2$ capsules.

The effect of all combinations of the T and $E_2$ treatments is illustrated in FIG. 1. It will be noted that 1.0 CM T-0.1 CM $E_2$ capsules resulted in a paired testis weight of 1.4 g, equivalent to that achieved with 4.0 CM T-O CM $E_2$ treatment. Moreover, 1.0 CM T-0.3 CM $E_2$ capsules causes an even greater diminution in paired testes weight (0.7 g). These results indicate that the testosterone and estradiol interact synergistically to suppress spermatogenesis.

The effect of the testosterone-estradiol treatments of Example 2 upon spermatozoa productions by rat testes $(\times 10^{-6})$ is shown in Table 4.

control to $17 \times 10^6$ for animals receiving 4.0 CM T capsules and increasing to $157 \times 10^6$ for animals receiving 12 CM T capsules (Table 4). The spermatozoa numbers per rat testis declined from $234 \times 10^6$ for control to 0 for rats receiving the 6 CM $E_2$ capsules (Table 4).

Figure 2:
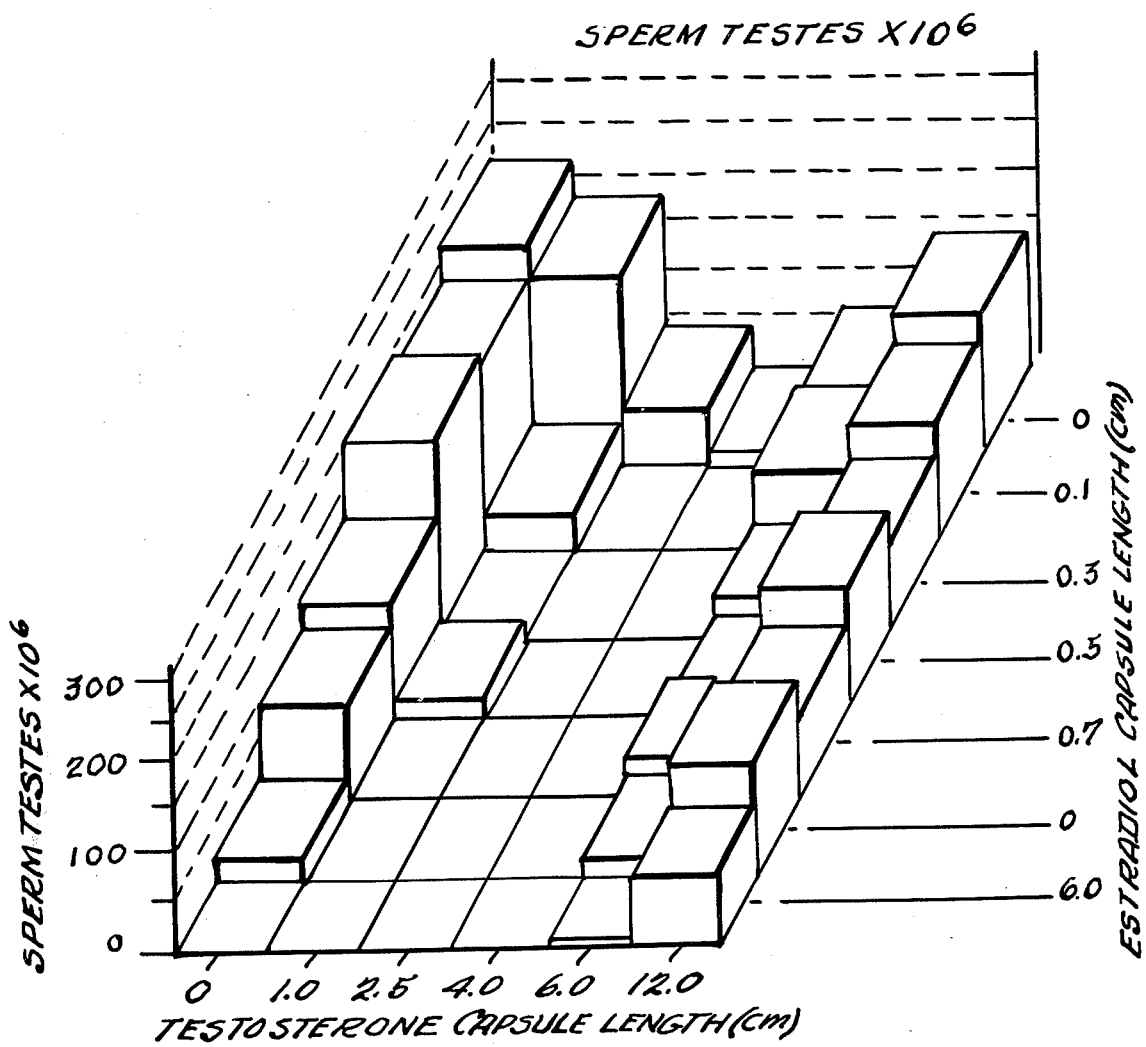
Figure 3:
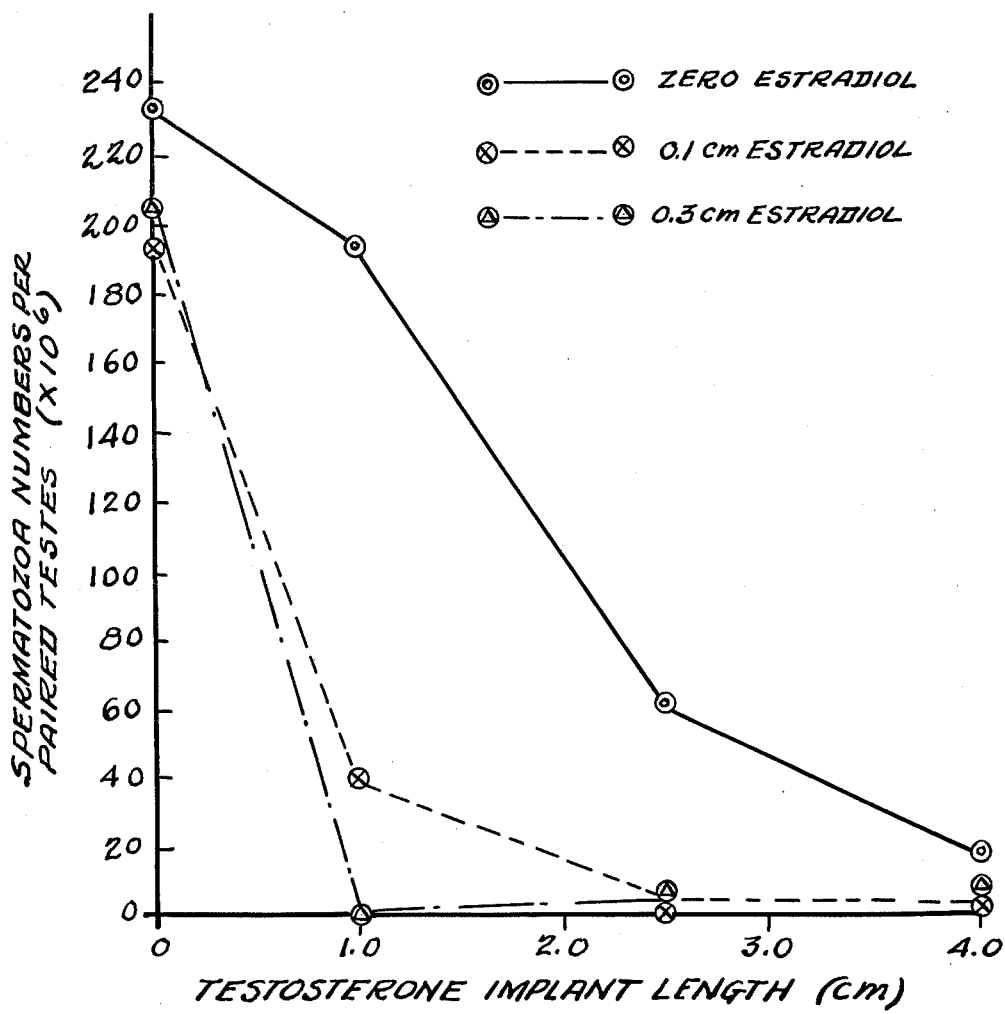

The effect of all combinations of T and $E_2$ treatments in Example 2 is evident from FIG. 2. In this connection, it should be noted that, as with testis weight, T and $E_2$ interact to produce a greater diminution in testicular spermatozoa numbers than either treatment alone and a greater diminution than the sum of the two treatments. For example, 2.5 CM T-0.1 CM $E_2$ capsules produced testes with only $0.6 \times 10^6$ spermatozoa per paired testes whereas 2.5 CM T alone gave $61 \times 10^6$ and 0.1 CM $E_2$ alone $194 \times 10^6$ spermatozoa per paired tests (Table 4). This synergistic effect can best be seen in FIG. 3 which shows the effect of three different testosterone-estradiol formulations upon spermatogenesis. It is evident from FIG. 3 and Table 4 that 0.1 and 0.3 CM $E_2$ capsules exert little direct effect upon spermatogenesis and yet when combined with 1.0 and 2.5 CM T capsules they dramatically reduced spermatogenesis obtained with T capsules alone.

Table 4

| Estradiol Implant Length (CM) | Testosterone Implant Length (CM) | | | | | |
|---|---|---|---|---|---|---|
| | 0 | 1.0 | 2.5 | 4.0 | 6.0 | 12.0 |
| 0 | 234 ± 12 | 193 ± 9 | 61 ± 39 | 17 ± 6 | 80 ± 19 | 157 ± 11 |
| 0.1 | 194 ± 18 | 38 ± 26 | 0.6 ± 0.2 | 3.8 ± 1.8 | 85 ± 7 | 130 ± 11 |
| 0.3 | 205 ± 15 | 0 | 0.3 ± 0.3 | 3.5 ± 1.4 | 43 ± 11 | 95 ± 29 |
| 0.5 | 125 ± 23 | 16 ± 14 | 0.6 ± 0.3 | 3.9 ± 1.7 | 14 ± 10 | 130 ± 5 |
| 0.7 | 105 ± 36 | 0 | 0 | 1.0 ± .3 | 41 ± 8 | 93 ± 23 |
| 1.0 | 24 ± 10 | 0 | 0 | 1.0 ± 0.1 | 26 ± 6 | 126 ± 10 |
| 6.0 | 0 | 0 | 0.1 ± 0.1 | 1.2 ± 1 | 5.4 ± 2.5 | 76 ± 16 |

It will be seen from Table 4 that the increase in testosterone dosages (0 through 12 CM capsules) gave the normal bisphasic response in spermatozoa number per rat testis, the number declining from $234 \times 10^6$ for the The effects of the testosterone and estradiol treatments on the spermatozoa numbers present in the caput-corpus epididymus and cauda epididymus $(\times 10^{-6})$ are shown in Tables 5 and 6, respectively.

Table 5

| Estradiol Implant Length (CM) | Testosterone Implant Length (CM) | | | | | |
|---|---|---|---|---|---|---|
| | 0 | 1.0 | 2.5 | 4.0 | 6.0 | 12.0 |
| 0 | 131 ± 1 | 127 ± 6 | 27 ± 20 | 0.9 ± 3 | 12 ± 6 | 80 ± 20 |
| 0.1 | 121 ± 8 | 22 ± 16 | 0.3 ± .3 | 0.6 ± .3 | 15 ± 5 | 75 ± 4 |
| 0.3 | 139 ± 10 | 0.2 ± 0.1 | 0 | 0.4 ± 0.2 | 7 ± 2 | 57 ± 16 |
| 0.5 | 81 ± 13 | 1.4 ± 1.3 | 0 | 0.3 ± 0.1 | 2.1 ± 1 | 85 ± 11 |
| 0.7 | 62 ± 30 | 1.2 ± 1.2 | 0.2 ± 0.2 | 0 | 5.9 ± 2.2 | 46 ± 14 |
| 1.0 | 0.7 ± 0.6 | 0 | 0 | 0.2 ± 0.2 | 0.9 ± 0.5 | 58 ± 16 |
| 6.0 | 0 | 0 | 0 | 0.2 ± 0.1 | 0.6 ± 0.4 | 30 ± 8 |

Table 6

| Estradiol Implant Length (CM) | Testosterone Implant Length (CM) | | | | | |
|---|---|---|---|---|---|---|
| | 0 | 1.0 | 2.5 | 4.0 | 6.0 | 12.0 |
| 0 | 147 ± 20 | 211 ± 17 | 61 ± 28 | 68 ± 6 | 91 ± 12 | 121 ± 12 |

Table 6-continued

| Estradiol Implant Length (CM) | Testosterone Implant Length (CM) | | | | | |
|---|---|---|---|---|---|---|
| | 0 | 1.0 | 2.5 | 4.0 | 6.0 | 12.0 |
| 0.1 | 137 ± 20 | 29 ± 11 | 50 ± 13 | 86 ± 23 | 98 ± 8 | 121 ± 17 |
| 0.3 | 120 ± 9 | 9 ± 2 | 20 ± 8 | 52 ± 11 | 73 ± 9 | 136 ± 21 |
| 0.5 | 62 ± 24 | 17 ± 7 | 63 ± 17 | 54 ± 9 | 69 ± 24 | 138 ± 21 |
| 0.7 | 62 ± 75 | 33 ± 14 | 37 ± 7 | 46 ± 16 | 68 ± 6 | 95 ± 18 |
| 1.0 | 1.8 ± 0.7 | 17 ± 0.3 | 47 ± 6 | 48 ± 8 | 70 ± 14 | 136 ± 22 |
| 6.0 | 0 | 18 ± 3 | 31 ± 4 | 32 ± 15 | 68 ± 19 | 105 ± 14 |

It will be noted that sperm numbers in the cauda epididymis declined less than those in either the testis or caput-corpus epididymis. The apparent maintenance of caudal epididymal spermatozoa numbers in apparently aspermatogenic rats is not surprising since it has been found that sperm storage in castrate rats is androgen dependent. Therefore, cauda epididymal spermatozoa numbers do not always reflect spermatogenic activity.

Table 7 shows the effects of the testosterone and estradiol treatments in Example 2 on LH and FSH concentration (ng/ml) in the serum of the rats.

A decline in serum LH concentration with increasing T and $E_2$ dosages is evident from Table 7. It also appears that the diminution in spermatogenesis is closely correlated with the disappearance of immunoreactive LH from peripheral blood (See Tables 4 and 7).

The effects of the testosterone-estradiol treatments of Example 2 upon seminal vesicle and ventral prostate weight (mgs) are shown in Tables 8 and 9, respectively.

Table 8

| Estradiol Implant Length (CM) | Testosterone Implant Length (CM) | | | | | |
|---|---|---|---|---|---|---|
| | 0 | 1.0 | 2.5 | 4.0 | 6.0 | 12.0 |
| 0 | 454 ± 8 | 384 ± 15 | 464 ± 26 | 532 ± 25 | 559 ± 17 | 716 ± 28 |
| 0.1 | 258 ± 28 | 316 ± 22 | 451 ± 21 | 566 ± 22 | 617 ± 39 | 702 ± 57 |
| 0.3 | 248 ± 29 | 350 ± 12 | 508 ± 28 | 639 ± 44 | 616 ± 22 | 739 ± 61 |
| 0.5 | 169 ± 14 | 316 ± 21 | 579 ± 28 | 599 ± 16 | 597 ± 33 | 703 ± 15 |
| 0.7 | 199 ± 39 | 315 ± 4 | 493 ± 17 | 623 ± 15 | 680 ± 13 | 739 ± 23 |
| 1.0 | 95 ± 10 | 284 ± 17 | 417 ± 20 | 635 ± 23 | 674 ± 46 | 710 ± 25 |
| 6.0 | 74 ± 10 | 271 ± 7 | 422 ± 19 | 596 ± 35 | 723 ± 47 | 879 ± 87 |

Table 9

| Estradiol Implant Length (CM) | Testosterone Implant Length (CM) | | | | | |
|---|---|---|---|---|---|---|
| | 0 | 1.0 | 2.5 | 4.0 | 6.0 | 12.0 |
| 0 | 577 ± 62 | 513 ± 66 | 687 ± 57 | 814 ± 48 | 893 ± 52 | 812 ± 59 |
| 0.1 | 358 ± 36 | 433 ± 31 | 678 ± 34 | 946 ± 28 | 855 ± 76 | 847 ± 27 |
| 0.3 | 286 ± 35 | 431 ± 25 | 617 ± 42 | 692 ± 93 | 905 ± 80 | 951 ± 75 |
| 0.5 | 172 ± 31 | 356 ± 31 | 652 ± 59 | 799 ± 60 | 663 ± 58 | 947 ± 56 |
| 0.7 | 169 ± 48 | 303 ± 24 | 522 ± 32 | 671 ± 72 | 819 ± 40 | 876 ± 65 |
| 1.0 | 81 ± 6 | 250 ± 17 | 510 ± 27 | 649 ± 64 | 701 ± 46 | 1066 ± 44 |
| 6.0 | 44 ± 9 | 266 ± 15 | 436 ± 21 | 575 ± 48 | 739 ± 42 | 847 ± 73 |

Table 7

| Estradiol Implant Length (CM) | | Testosterone Implant Length (CM) | | | | | |
|---|---|---|---|---|---|---|---|
| | | 0 | 1.0 | 2.5 | 4.0 | 6.0 | 12.0 |
| 0 | LH | 8.0 ± 1.0 | 2.4 ± 0.3 | 2.9 ± 0.3 | ND | ND | ND |
| | FSH | 409 ± 98 | 269 ± 13 | 234 ± 24 | 218 ± 7 | 223 ± 7 | 291 ± 26 |
| 0.1 | LH | 2.8 ± | ND | ND | ND | ND | ND |
| | FSH | 294 ± 22 | 294 ± 36 | 283 ± 10 | 259 ± 21 | 258 ± 20 | 282 ± 9 |
| 0.3 | LH | ND | ND | ND | ND | ND | ND |
| | FSH | 408 ± 24 | 354 ± 39 | 351 ± 42 | 287 ± 9 | 254 ± 20 | 292 ± 14 |
| 0.5 | LH | ND | ND | ND | ND | ND | ND |
| | FSH | 407 ± 40 | 345 ± 25 | 279 ± 19 | 244 ± 15 | 321 ± 21 | 267 ± 41 |
| 0.7 | LH | ND | ND | ND | ND | ND | ND |
| | FSH | 379 ± 28 | 368 ± 69 | 246 ± 8 | 264 ± 6 | 242 ± 12 | 302 ± 17 |
| 1.0 | LH | ND | ND | ND | ND | ND | ND |
| | FSH | 283 ± 24 | 230 ± 14 | 258 ± 15 | 403 ± 19 | 268 ± 23 | 356 ± 95 |
| 6.0 | LH | ND | ND | ND | ND | ND | ND |
| | FSH | 184 ± 28 | 185 ± 6 | 196 ± 26 | 260 ± | 282 ± | 293 ± 26 |

Table 7 shows that the serum FSH concentration was suppressed by both testosterone and estradiol treatments. However, no interaction effect between testosterone and estradiol upon the serum FSH concentration is evident from the results given in Table 7.

It will be evident from Tables 8 and 9 that increasing testosterone dosage (0 through 12 CM) resulted in an increase in both seminal vesicle and prostate weight, while increasing estradiol dosage (0 through 6 CM) resulted in diminution in both seminal vesicle and ventral prostate weight.

Figure 4:
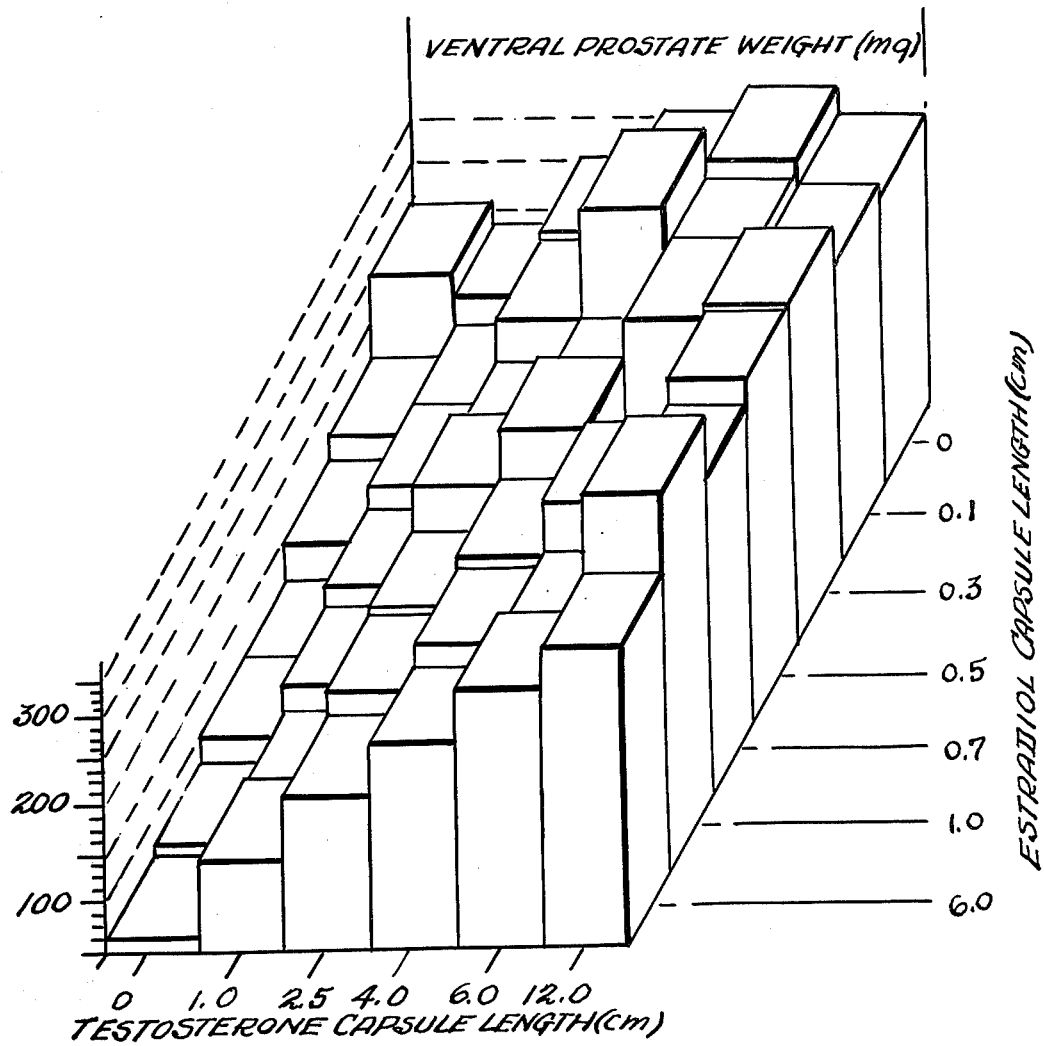

The effect of T-$E_2$ upon ventral prostate weight can best be seen in FIG. 4. In general, it can be stated that estradiol does not antagonize the stimulatory effect of testosterone upon seminal vesicle and ventral prostate growth. Moreover, it appears that some T/$E_2$ formulations induce azoospermia without increasing either seminal vesicle or ventral prostage weight. For example, 1.0 CM T-0.3 CM $E_2$ caused azoospermia (FIG. 3) but did not increase accessory sex organ size (FIG. 4).

It is to be noted that Example 2 includes an expansion of experimental work reported in Example 1. Hence there is some duplication in the results reported in the two examples (Compare, for instance, Tables 1 and 4).

EXAMPLE 3

Further test results using testosterone (T) and estradiol (E) polydimethylsiloxane subdermal implants as described above on male rats are shown below:

Table 10

| Criterion | Control | 4.0 cm T | 2.5 cm T | 2.5 cm T-0.1 cm E2 |
|---|---|---|---|---|
| [1]Testis weight (gs) | 3.4 ± 0.09 | 1.5 ± 0.08 | 1.6 ± 0.3 | 1.0 ± 0.02 |
| [1]Sperm Nos./rat testis ($\times 10^{-6}$) | 234 ± 12 | 17 ± 6 | 61 ± 39 | 0.6 ± 0.2 |
| [1]Seminal vesicle weight (mgs) | 454 ± 8 | 532 ± 25 | 464 ± 26 | 451 ± 21 |
| [1]Ventral prostate weight (mgs) | 577 ± 62 | 814 ± 48 | 687 ± 57 | 678 ± 34 |
| [1]LH in serum (ng/ml) | 8.0 ± 1.0 | N.D.* | 2.9 ± 0.3 | N.D. |
| [1]FSH in serum (ng/ml) | 409 ± 98 | 218 ± 7 | 234 ± 24 | 283 ± 10 |
| [1]Estradiol in serum (pg/ml) | 45.8 ± 10.7 | 40.6 ± 5.0 | 48.0 ± 13 | 42.7 ± 4.0 |
| [1]Testosterone in serum (ng/ml) | 2.5 ± 0.19 | 3.1 ± 0.44 | 3.0 ± 0.31 | 2.25 ± 0.05 |
| [2]Fertility | | | | |
| Fertile/Infertile (%) | 100 | 10 | 10 | 0 |
| [2]Embryos/5 females | 560 | 1 | 52 | 0 |

[1]Experiment 1: Each group received the implants for three months. They were then sacrificed and each criterion measured.
[2]Experiment 2: Each group received the implants for three months. Each group contained ten males. Each male was then placed with five proven breeder females for three weeks. Females were sacrificed and embryos, implantation sites, and corpora lutea were counted.
*Non-detectable.

As indicated in Table 10, complete infertility was obtained using the combination of a 2.5 cm T implant and a 0.1 cm $E_2$ implant.

It will be evident from the foregoing that the present invention offers an effective systemic contraceptive method for use by the human male. Others have previously tried to accomplish male contraception by means of the systemic administration of androgenic steroids but such prior treatments have failed to induce azoospermia in all of the treated individuals (see *Fertil. Steril.*, 1, 415–422, (1950); *The Human Testis*, ed. by Rosenburg and Paulsen, 249–257, Plenum, New York, 1970; *Contraception*, 10, 281–289, (1974); and *Regulatory Mechanisms of Male Reproductive Physiology*, 197–211 (Excerpta Medica, Amsterdam 1976). To overcome this major difficulty, androgen-progestin formulations were also tested previously. However, such attempts did not inhibit spermatogenesis completely in all treated men (see *Contraception*, 8, 207–212, (1973); *Contraception*, 8, 191–206, (1973); *Control of Male Fertility*, 230–239, Harper and Row, Hagerstown, Md. 1975; and *Contraception*, 8, 219–226 (1973). The present invention, in contrast to prior methods involving systemic adminstration, appears to make possible the complete inhibition of spermatogenesis. Apparently the prior effects have failed because of at least two problems: (1) the relatively weak antigonadotropic activity of both androgens and progestins and (2) the difficulty in precisely controlling the dosage of steroids administered. The invention avoids these problems by providing for the continuous administration of the steroids at relatively constant rates using a sustained release capsule and by substituting estradiol, a compound known to be a potent inhibitor of pituitary gonadotropin secretion, for the progestins.

As a further aspect of the invention, it is noted that the capsule of the invention containing androgen and estrogen would be expected to enhance libido or sex drive in the aging male. This may be exemplified as follows:

EXAMPLE 4

When aged rats are divided into two equal groups and Silastic capsules containing no steroidal hormones implanted in one group of rats and Silastic capsules containing a mixture of testosterone and estradiol-17β implanted in the other group of rats, the rats having the steroid filled implants are found to be more sexually active than those having the empty implants. Similar results would be obtained in the case where the androgen and the estrogen are implanted in separate capsules.

Various modifications may be made in the invention as described herein. Hence, the scope of the invention is defined in the following claims wherein:

We claim:

1. A method of affecting male contraception which comprises subdermally implanting in the male a contraceptively effective amount of a synergistically active mixture of an androgen and an estrogen in one or more slow release capsules, the ratio of androgen to estrogen being in the range of 250 to 1 and 500 to 1, and permitting the androgen and estrogen to be continuously released at relatively constant rates for the desired length of time, said method being characterized by providing effective contraception without chronic elevation of the androgen and estrogen content in the peripheral blood.

2. The method of claim 1 wherein the androgen is testosterone and the estrogen is estradiol and these are implanted in separate slow release capsules.

3. A contraceptive product comprising a synergistic combination of a contraceptively effective amount of testosterone and estradiol in the same or separate slow release capsules suitable for subdermal implantation such that the testosterone and estradiol are continuously released at relatively constant rates, the ratio of testosterone to estradiol being in the range of 250 to 1 and 500 to 1 and the product being further characterized by providing effective contraception without chronic elevation of the androgen and estrogen content in the peripheral blood.

4. A method of enhancing sexual libido in an aging male which comprises subdermally implanting in said male a libido-enhancing amount of a synergistically active mixture of an androgen and an estrogen in one or more slow release capsules, the ratio of androgen to estrogen being in the range of 250 to 1 and 500 to 1, and permitting the androgen and estrogen to be continuously released at relatively constant rates for the desired length of time.

5. The method of claim 4 wherein the androgen is testosterone and the estrogen is estradiol and these are implanted in separate slow release capsules.

6. A product for enhancing sexual libido in the aging male comprising a synergistic combination of a libido-enhancing amount of testosterone and estradiol in the same or separate slow release capsules suitable for subdermal implantation, such that the testosterone and estradiol are continuously released at relatively constant rates, the ratio of testosterone to estradiol being in the range of 250 to 1 and 500 to 1.

* * * * *